United States Patent [19]

Lindig et al.

[11] Patent Number: 4,822,810

[45] Date of Patent: Apr. 18, 1989

[54] 1-ARALKYL-5-IMINO-PYRAZOLE COMPOUNDS, PESTICIDAL COMPOSITION AND USE

[75] Inventors: Markus Lindig, Hilden; Benedikt Becker, Mettmann, both of Fed. Rep. of Germany

[73] Assignee: Bayer Aktiengesellschaft, Leverkusen, Fed. Rep. of Germany

[21] Appl. No.: 175,380

[22] Filed: Mar. 30, 1988

[30] Foreign Application Priority Data

Apr. 9, 1987 [DE] Fed. Rep. of Germany ....... 3712072

[51] Int. Cl.$^4$ .................... A01N 43/56; C07D 231/52
[52] U.S. Cl. ........................................ 514/407; 71/92;
548/376
[58] Field of Search ......................... 548/376; 514/407

[56] References Cited

U.S. PATENT DOCUMENTS 4,370,339  1/1983  Haviv et al. ..................... 548/362
4,740,232  4/1988  Gehring et al. ..................... 548/374

Primary Examiner—Robert W. Ramsuer
Attorney, Agent, or Firm—Sprung Horn Kramer & Woods

[57] ABSTRACT

Arthropodicidally active 1-aralkylpyrazoles of the formula

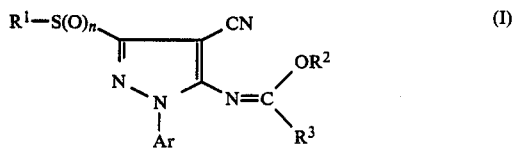

in which
  $R^1$ represents alkyl,
  $R^2$ represents alkyl,
  $R^3$ represents hydrogen or alkyl,
  Ar represents optionally substituted aralkyl and
  n represents the numbers 0, 1 or 2.

9 Claims, No Drawings

1-ARALKYL-5-IMINO-PYRAZOLE COMPOUNDS, PESTICIDAL COMPOSITION AND USE

The present invention relates to new 1-aralkyl-pyrazoles, a process for their preparation and their use as agents for combating pests.

It is already known that pyrazole derivaties, such as, for example, 1-cyclohexyl-5-[N,N-(dimethyl)-carbamoyloxy]-3-methylthiomethyl-pyrazole, 1-cyclohexyl-5-[N,N-(dimethyl)-carbamoyloxy]-3-methylsulphinylmethyl-pyrazole or 1-cyclohexyl-5-[N,N-(dimethyl)-carbamoyloxy]-3-methylsulphonylmethyl-pyrazole, have pesticidal properties (compare, for example, DE-OS (German Published Specification) No. 2,839,270).

However, the level of action and duration of action of these compounds are not always completely satisfactory, especially against certain harmful organisms or when low concentrations are applied.

New 1-aralkylpyrazoles of the general formula (I)

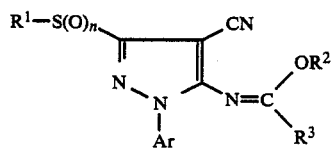

(I)

in which
R$^1$ represents alkyl,
R$^2$ represents alkyl,
R$^3$ represents hydrogen or alkyl,
Ar represents optionally substituted aralkyl and
n represents the numbers 0, 1 or 2,
have been found.

It has furthermore been found that the new 1-aralkyl-pyrazoles of the general formula (I)

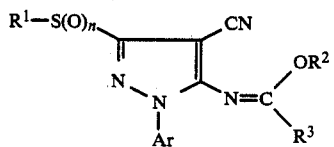

(I)

in which
R$^1$ represents alkyl,
R$^2$ represents alkyl,
R$^3$ represents hydrogen or alkyl,
Ar represents optionally substituted aralkyl and
n represents the numbers 0, 1 or 2,
are obtained by a process in which 5-amino-1-aralkyl-pyrazoles of the formula (II)

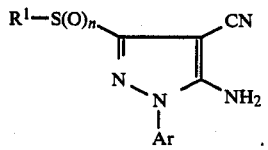

(II)

in which
R$^1$, Ar and n have the abovementioned meaning,
are reacted with orthoesters of the formula (III)

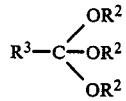

(III)

in which
R$^2$ and R$^3$ have the abovementioned meaning,
if appropriate in the presence of a diluent.

Finally, it has been found that the new 1-aralkyl-pyrazoles of the general formula (I) have pesticidal properties, in particular acaricidal properties.

Surprisingly, the 1-aralkylpyrazoles of the general formula (I) according to the invention exhibit a considerably better acaricidal activity than the pyrazole derivatives known from the prior art, such as, for example, the compounds 1-cyclohexyl-5-[N,N-(dimethyl)-carbamoyloxy]-3-methylthiomethyl-pyrazole, 1-cyclohexyl-5-[N,N-(dimethyl)-carbamoyloxy]-3-methylsulphinylmethyl-pyrazole and 1-cyclohexyl-5-[N,N-(dimethyl)-carbamoyloxy]-3-methylsulphonylmethyl-pyrazole which are closely related compounds chemically and from the point of view of their action.

Formula (I) provides a general definition of the 1-aralkylpyrazoles according to the invention. Preferred compounds of the formula (I) are those in which
R$^1$ represents straight-chain or branched alkyl with 1 to 8 carbon atoms,
R$^2$ represents straight-chain or branched alkyl with 1 to 8 carbon atoms,
R$^3$ represents hydrogen, or represents straight-chain or branched alkyl with 1 to 8 carbon atoms,
Ar represents phenylalkyl which has 1 to 4 carbon atoms in the straight-chain or branched alkyl part and is optionally substituted by one or more identical or different substituents, substituents of the phenyl radical which may be mentioned being: halogen, halogenoalkyl and halogenoalkoxy with in each case 1 to 2 carbon atoms, and 1 to 5 identical or different halogen atoms, and
n represents a number 0, 1 or 2.

Particularly preferred 1-aralkylpyrazoles of the formula (I) are those in which
R$^1$ represents methyl, ethyl, n- or i-propyl, or n-, i-, s- or t-butyl,
R$^2$ represents methyl, ethyl, n- or i-propyl, or n-, i-, s- or t-butyl,
R$^3$ represents hydrogen, methyl, ethyl, n- or i-propyl, or n-, i-, s- or t-butyl,
Ar represents benzyl, 1-phenethyl or 2-phenethyl, in each case optionally substituted by one to three identical or different substituents from the group comprising fluorine, chlorine, trifluoromethyl and trifluoromethoxy, and
n represents a number 0, 1 or 2.

The following 1-aralkylpyrazoles of the general formula (I) may be mentioned specifically, in addition to the compounds mentioned in the preparation examples:

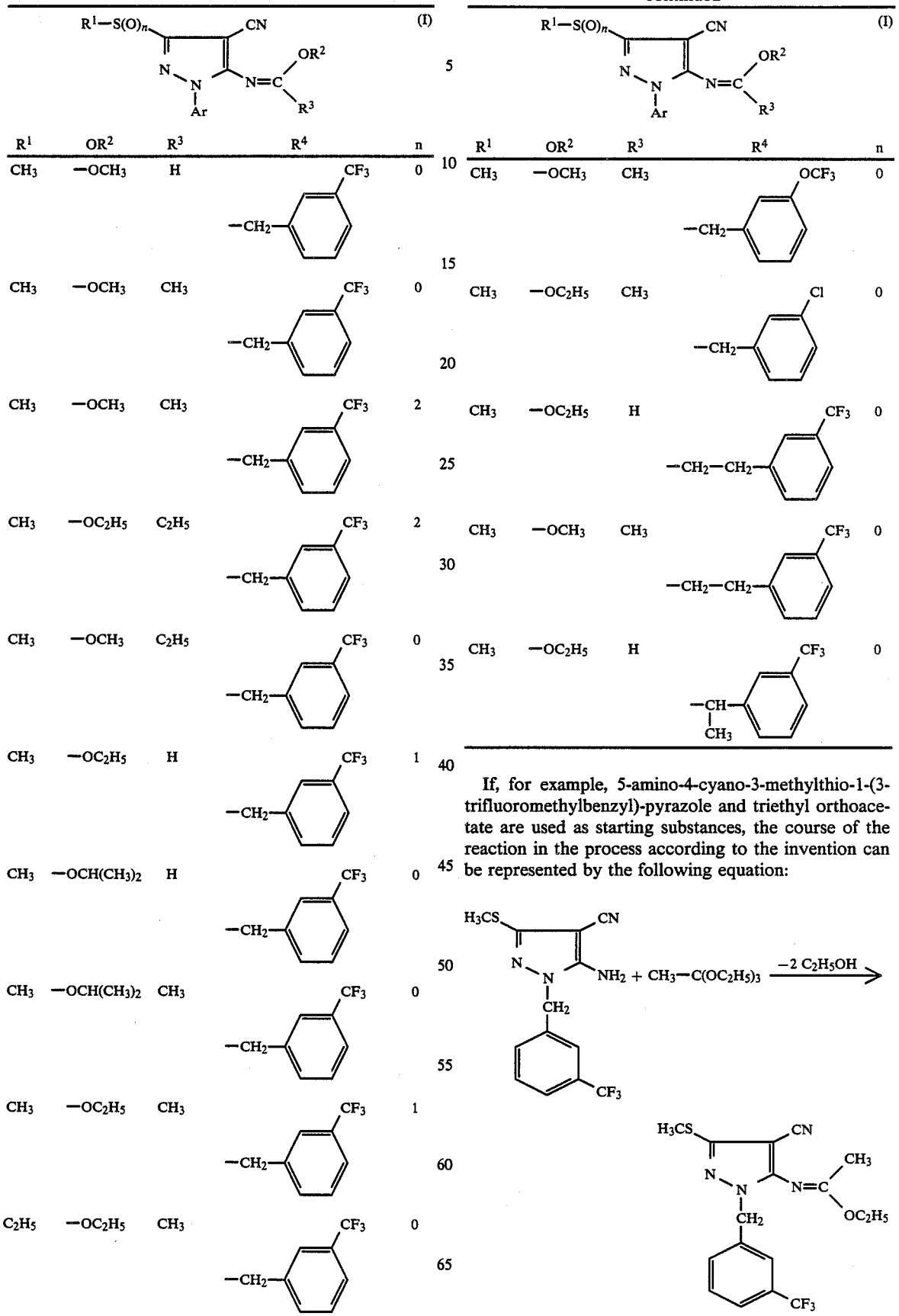
If, for example, 5-amino-4-cyano-3-methylthio-1-(3-trifluoromethylbenzyl)-pyrazole and triethyl orthoacetate are used as starting substances, the course of the reaction in the process according to the invention can be represented by the following equation:
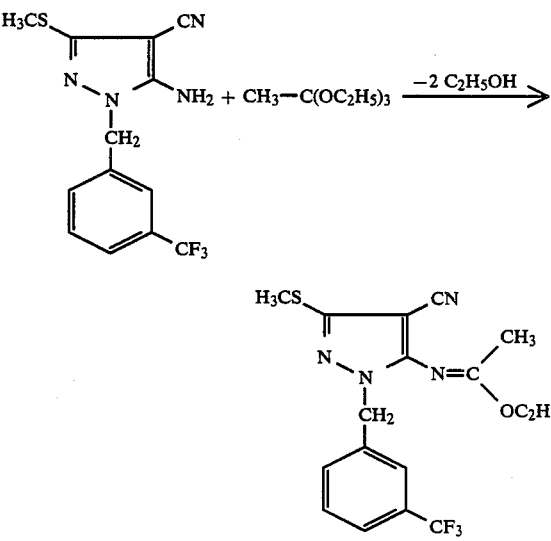

Formula (II) provides a general definition of the 5-amino-1-aralkylpyrazoles required as starting substances for carrying out the process according to the invention. In this formula (II), $R^1$, Ar and n preferably represent those radicals and indices which have already been mentioned as preferred for these substituents and this index in connection with the description of the substances of the formula (I) according to the invention.

The 5-amino-1-aralkylpyrazoles of the formula (II) are the subject of German patent application No. P 36 16 618; corresponding to U.S. application Ser. No. 049,748, filed May 13, 1987, now pending. They are obtained by a process in which aralkylhydrazines of the formula (IV)

$$Ar-NH-NH_2 \qquad (IV)$$

in which

Ar has the abovementioned meaning,
or acid addition salts thereof, are reacted with dinitriles of the formula (V)

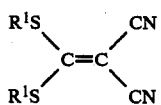

in which $R^1$ has the abovementioned meaning,
if appropriate in the presence of a diluent, such as, for example, ethanol, at temperatures between 0° C. and 60° C., and if appropriate, the 3-alkylthio-5-amino-1-aralkylpyrazoles thus obtainable, of the formula (IIa)

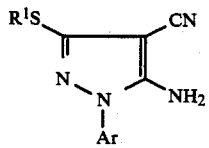

in which $R^1$ and Ar have the abovementioned meaning,
are oxidized on the sulphur in the 3-position of the pyrazole ring with customary oxidizing agents, such as, for example, m-chloroperbenzoic acid, if appropriate in the presence of a diluent, such as, for example, chloroform, at temperatures between 0° C. and 40° C.

The aralkylhydrazines of the formula (IV) or their acid addition salts, such as, for example, hydrochlorides, are known (compare, for example, DE-OS (German Published Specification) No. 2,230,675 or U.S. Pat. No. 4,370,339), or they are obtainable by processes analogous to known processes.

The dinitriles of the formula (V) are likewise known (compare, for example, Chem. Ber. 95, 2861, 2871 [1962]; Arch. Pharm. 314, 817-823 [1981]; Tetrahedron 30, 3181-3184 [1974] or DE-OS (German Published Specification) No. 3,217,931).

Formula (III) provides a general definition of the orthoesters furthermore required as starting substances for carrying out the process according to the invention. In this formula (III), $R^2$ and $R^3$ preferably represent those radicals which have already been mentioned as preferred for these substituents in connection with the description of the substances of the formula (I) according to the invention.

The orthoesters of the formula (III) are generally known compounds of organic chemistry.

Possible diluents for carrying out the process according to the invention are inert organic solvents.

These include, in particular, aliphatic, alicyclic or aromatic, optionally halogenated hydrocarbons, such as, for example, benzine, benzene, toluene, xylene, chlorobenzene, petroleum ether, hexane, cyclohexane, methylene chloride, chloroform and carbon tetrachloride, ethers, such as diethyl ether, dioxane, tetrahydrofuran or ethylene glycol dimethyl or diethyl ether, nitriles, such as acetonitrile or propionitrile, or amides, such as dimethylformamide, dimethylacetamide, N-methylformanilide, N-methylpyrrolidone or hexamethylphosphoric acid triamide.

However, it is also possible for the orthoesters of the formula (III) employed as reactants also to be employed simultaneously as the diluents in an appropriate excess.

The reaction temperatures can be varied within a substantial range in carrying out the process according to the invention. The reaction is in general carried out at temperatures between 20° C. and 150° C., preferably at temperatures between 50° C. and 120° C.

For carrying out the process according to the invention, in general 1.0 to 30.0 mols, preferably 1.0 to 15.0 mols of orthoester of the formula (III) are employed per mol of 5-amino-1-aralkylpyrazole of the formula (II).

The reaction is carried out and the reaction products are worked up and isolated by generally customary methods.

The active compounds are suitable for combating animal pests, preferably arthropods and in particular insects and arachnida, encountered in agriculture, in forestry, in the protection of stored products and of materials, and in the hygiene field. They are active against normally sensitive and resistant species and against all or some stages of development. The abovementioned pests include:

From the order of Isopoda, for example, *Oniscus asellus, Armadillidium vulgare* and *Porcellio scaber.* From the order of the Diplopoda, for example, *Blaniulus guttulatus.* From the order of the Chilopoda, for example, *Geophilus carpophagus* and Scutigera spec. From the order of the Symphyla, for example, *Scutigerella immaculata.* From the order of the Thysanura, for example, *Lepisma saccharina.* From the order of the Collembola, for example, *Onychiurus armatus.* From the order of the Orthoptera, for example, *Blatta orientalis, Periplaneta americanna, Leucophaea maderae, Blattella germanica, Acheta domesticus,* Gryllotalpa spp., *Locusta migratoria migratorioides, Melanoplus differentialis* and *Schistocerca gregaria.* From the order of the Dermaptera, for example, *Forficula auricularia.* From the order of the Isoptera, for example, Reticulitermes spp. From the order of the Anoplura, for example, *Phylloxera vastatrix,* Pemphigus spp., *Pediculus humanus corporis,* Haemetopinus spp. and Linognathus spp. From the order of the Mallophaga, for example, Trichodectes spp. and Damalinea spp. From the order of Thysanoptera, for example, *Hercinothrips femoralis* and *Thrips tabaci.* From the order of the Heteroptera, for example, Eurygaster spp., *Dysdercus intermedius, Piesma quadrata, Cimex lectularius, Rhodnius prolixus* and Triatoma spp. From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus arundinis, Macrosiphum avenae,* Myzus spp., *Phorodon humuli, Rhopalosiphum padi*, Empoasca spp., *Euscelis bilobatus, Nephotettix cincticeps, Lecanium corni, Saissetia oleae, Laodelphax stritallus, Nilaparvata lugens, Aonidiella aurantii, Aspidiotus hederae*, Pseudococcus spp. and Psylla spp. From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea*, Lymantria spp. *Bucculatrix thurberiella, Phyllocnistis citrella*, Agrotis spp., Euxoa spp., Feltia spp., *Earias insulana*, Heliothis spp., *Spodoptera exigua, Mamestra brassicae, Panolis flammea, Prodenia litura*, Spodoptera spp., *Trichoplusia ni, Carpocapsa pomonella*, Pieris spp., Chilo spp., *Pyrausta nubilalis, Ephestia kuehniella, Galleria mellonella, Tineola bisselliella, Tinea pellionella, Hofmannophila pseudopretella, Cacoecia podana, Capua reticulana, Choristoneura fumiferana, Clysia ambiguella, Homona magnanima* and *Tortrix viridana*. From the order of the Coleoptera, for example, *Anobium punctatum, Rhizopertha dominica, Acanthoscelides obtectus, Hylotrupes bajulus, Agelastica alni, Leptinotarsa decemlineata, Phaedon cochleariae*, Diabrotica spp., *Psylliodes chrysocphala, Epilachna varive stis*, Atomaria spp., *Oryzaephilus surinamensis*, Antho nomus spp., Sitophilus spp., *Otiorrhynchus sulcatus, Cosmopolites sordidus, Ceuthorrhynchus assimilis, Hypera postica*, Dermestes spp., Trogoderma spp., Anthrenus spp., Attagenus spp., Lyctus spp., *Meligethes aeneus*, Ptinus spp., *Niptus hololeucus, Gibbium psylloides*, Tribolium spp., *Tenebrio molitor*, Agriotes spp., Conoderus spp., *Melolontha melolontha, Amphimallon solstitialis* and Costelytra zealandica. From the order of the Hymenoptera, for example, Diprion spp., Hoplocampa spp., Lasius spp., *Monomorium pharaonis* and Vespa spp. From the order of the Diptera, for example, Aedes spp., Anopheles spp., Culex spp., *Drosophila melanogaster*, Musca spp., Fannia spp., *Calliphora erythrocephala*, Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit*, Phorbia spp., *Pegomyia hyoscyami, Ceratitis capitata, Dacus oleae* and *Tipula paludosa*. From the order of the Siphonaptera, for example, *Xenopsylla cheopis* and Ceratophyllus spp. From the order of the Arachnida, for example, *Scorpio maurus* and *Latrodectus mactans*. From the order of the Acarina, for example, *Acarus siro*, Argas spp., Ornithodoros spp., *Dermanyssus gallinae, Eriophyes ribis, Phyllocoptruta oleivora*, Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa*, Panonychus spp., Tetranychus spp.

The active compounds according to the invention can thereby be used with particularly good success for combating the common spider mite (*Tetranychus urticae*).

Depending on their particular physical and/or chemical properties, the active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and furthermore formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surfaceactive agents, that is emusifying agents and/or dispersing agents and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly dispersed silicic acid, alumina and silicates; as solid carriers for granules there are suitable: for example crushed and fractioned natural rocks such as calcite, marble, pumice, sepiolite and dolomite, as well as synthetic granules of inorganic and organic meals, and granules of organic materials such as sawdust, coconut shells, corn cobs and tobacco stalks; as emuslifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in their commercially available formulations and in the use forms, prepared from these formulations, as a mixture with other active compounds, such as insecticides, baits, sterilizing agents, acaricides, nematicides, fungicides, growth-regulating substances or herbicides. The insecticides include, for example, phosphates, carbamates, carboxylates, chlorinated hydrocarbons, phenylureas and substances produced by microorganisms, inter alia.

The active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

Application takes place in a customary manner appropriate for the use forms.

PREPARATION EXAMPLES

Example 1

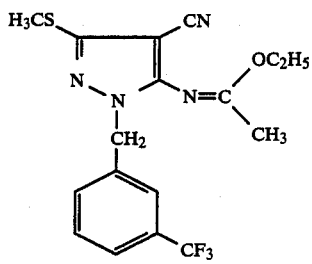

6 g (0.019 mol) of 5-amino-4-cyano-3-methylthio-1-(3-trifluoromethylbenzyl)-pyrazole and 20 ml (17.7 g=0.11 mol) of triethyl orthoacetate are stirred at the reflux temperature for 3 hours. For working up, the mixture is concentrated in vacuo and the residue is made to crystallize by trituration with petroleum ether. 6.0 g (83% of theory) of 4-cyano-3-methylthio-1-(3-trifluoromethylbenzyl-5-(1-ethoxyethylideneimino)-pyrazole of melting point 65° C. are obtained.

Preparation of the Starting Compound

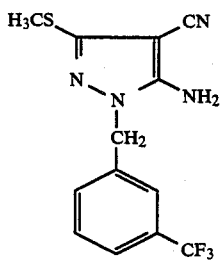

8.5 g (0.05 mol) of 1,1-dicyano-2,2-bis(methylthio)-ethylene and 9.5 g (0.06 mol) of 3-trifluoromethylbenzyl-hydrazine (compare DE-OS (German Published Specification) No. 2,230,675) are stirred in 100 ml of ethanol at 20° C. for 15 hours. For working up, the solvent is removed in vacuo and the residue is triturated with petroleum ether. Filtration with suction gives 12.4 g (80% of theory) of 5-amino-4-cyano-3-methylthio-1-(3-trifluoromethylbenzyl)-pyrazole of melting point 142° C.

The following 1-aralkylpyrazoles of the general formula (I) are obtained in a corresponding manner and in accordance with the general statements on the preparation:

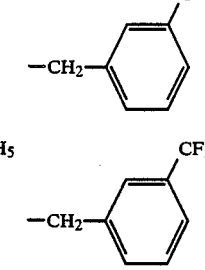

| Example No. | $R^1$ | $OR^2$ | $R^3$ | Ar | n | Melting point/°C. |
|---|---|---|---|---|---|---|
| 2 | $CH_3$ | $-OC_2H_5$ | H | $-CH_2-\phi-CF_3$ | 0 | 82 |
| 3 | $CH_3$ | $-OC_2H_3$ | $C_2H_5$ | $-CH_2-\phi-CF_3$ | 0 | 54 |

Use Examples

The compounds shown below were used as comparison substances in the use example with follows:

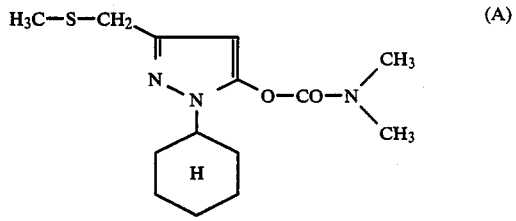

1-Cyclohexyl-5-(N,N-dimethylcarbamoyloxy)-4-methylthiomethyl-pyrazole

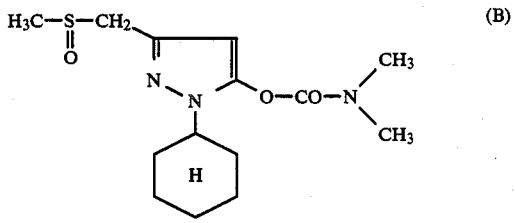

1-Cyclohexyl-5-(N,N-dimethylcarbamoyloxy)-3-methylsulphinylmethyl-pyrazole

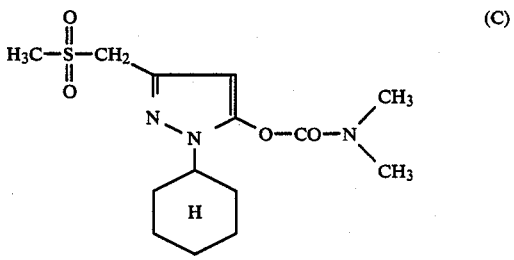

1-Cyclohexyl-5-(N,N-dimethylcarbamoyloxy)-3-methylsulphonylmethyl-pyrazole (all known from DE-OS (German Published Specification) No. 2,839,270).

Example A

Tetranychus test (resistant
Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the state amount of emulsifier, and the concentrate is diluted with water to the desired concentration.

Bean plants (*Phaseolus vulgaris*) which are heavily infested with the common spider mite or two-spotted spider mite (*Tetranychus urticae*) in all stages of development are treated by being dipped into the preparation of the active compound of the desired concentration.

After the specified periods of time, the destruction in % is determined. 100% means that all the spider mites have been killed; 0% means that none of the spider mites have been killed.

In this test, for example, the following compounds from the preparation examples show a superior activity compared with the prior art: 1, 2 and 3.

It will be understood that the specification and examples are illustrative but not limitative of the present invention and that other embodiments within the spirit and scope of the invention will suggest themselves to those skilled in the art.

We claim:

1. A 1-aralkylpyrazole of the formula

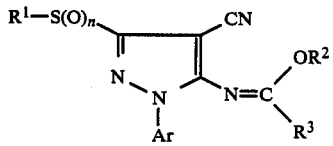

(I)

in which
R$^1$ represents alkyl,
R$^2$ represents alkyl,
R$^3$ represents hydrogen or alkyl,
Ar represents optionally substituted aralkyl and
n represents the numbers 0, 1 or 2.

2. A 1-aralkylpyrazole according to claim 1, in which
R$^1$ represents straight-chain or branched alkyl with 1 to 8 carbon atoms,
R$^2$ represents straight-chain or branched alkyl with 1 to 8 carbon atoms,
R$^3$ represents hydrogen, or represents straight-chain or branched alkyl with 1 to 8 carbon atoms, and
Ar represents phenylalkyl which has 1 to 4 carbon atoms in the straight-chain or branched alkyl part and is optionally substituted by one or more identical or different substituents.

3. A 1-aralkylpyrazole according to claim 1, in which
R$^1$ represents methyl, ethyl, n- or i-propyl, or n-, i-, s- or t-butyl,
R$^2$ represents methyl, ethyl, n- or i-propyl, or n-, i-, s- or t-butyl,
R$^3$ represents hyrdrogen, methyl, ethyl, n- or i-propyl, or n-, i-, s- or t-butyl, and
Ar represents benzyl, 1-phenethyl or 2-phenethyl, in each case optionally substituted by one to three identical or different substituents from the group consisting of fluorine, chlorine, trifluoromethyl and trifluoromethoxy.

4. A 1-aralkylpyrazole according to claim 1, wherein such compound is 4-cyano-3-methylthio-1-(3-trifluoromethylbenzyl)-5-(1-ethoxyethylideneimino)-pyrazole of the formula

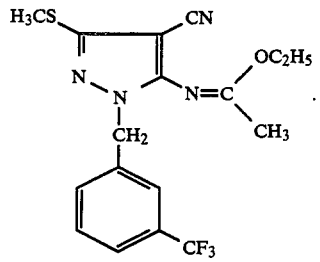

5. A 1-aralkylpyrazole according to claim 1, wherein such compound is 4-cyano-3-methylthio-1-(3-trifluoromethylbenzyl)-5-(1-ethoxymethylideneimino)-pyrazole of the formula

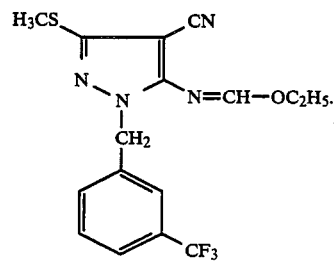

6. A 1-aralkylpyrazole according to claim 1, wherein such compound is 4-cyano-3-methylthio-1-(3-trifluoromethylbenzyl)-5-(1-ethoxypropylideneimino)-pyrazole of the formula

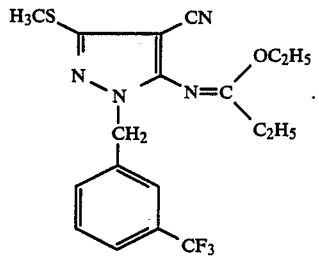

7. An arthropodicidal composition comprising an arthropodicidally effective amount of a compound according to claim 1 and a diluent.

8. A method of combating arthropods which comprises applying to such arthropods or to an arthropod habitat an arthropodicidally effective amount of a compound according to claim 1.

9. A method according to claim 8, wherein such compound is
4-cyano-3-methylthio-1-(3-trifluoromethylbenzyl)-5-(1-ethoxyethylideneimino)-pyrazole,
4-cyano-3-methylthio-1-(3-trifluoromethylbenzyl)-5-(1-ethoxymethylideneimino)-pyrazole or
4-cyano-3-methylthio-1-(3-trifluoromethylbenzyl)-5-(1ethoxypropylideneimino)-pyrazole.

* * * * *

UNITED STATES PATENT AND TRADEMARK OFFICE
CERTIFICATE OF CORRECTION

PATENT NO. : 4,822,810

DATED : April 18, 1989

INVENTOR(S) : Lindig Markus, et al

It is certified that error appears in the above-identified patent and that said Letters Patent is hereby corrected as shown below:

Col.12, line 67      Delete "(lethoxypropylideneimino)" and substitute --(1-ethoxypropylideneimino)--

Signed and Sealed this

Fifth Day of June, 1990

Attest:

HARRY F. MANBECK, JR.

*Attesting Officer*      *Commissioner of Patents and Trademarks*